Figure 1:
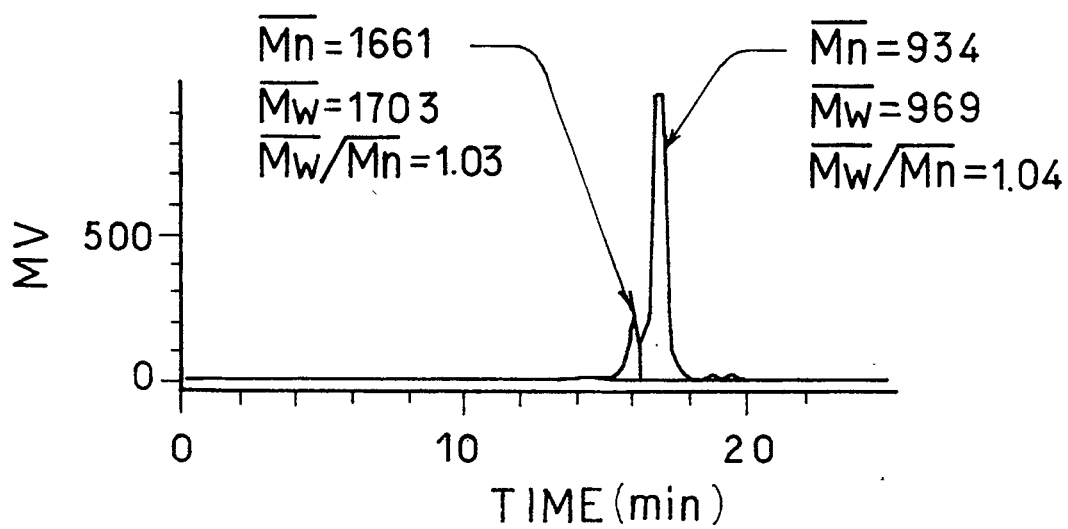

United States Patent [19]

Kobayashi et al.

[11] Patent Number: 5,356,566
[45] Date of Patent: Oct. 18, 1994

[54] POLYESTER COMPOUNDS AND ORGANIC GELLING AGENTS COMPRISING SAME

[75] Inventors: Toshiaki Kobayashi, Nara; Sachio Kitagawa, Yawata, both of Japan

[73] Assignee: New Japan Chemical Co., Ltd., Japan

[21] Appl. No.: 78,030

[22] Filed: Jun. 18, 1993

[30] Foreign Application Priority Data

Jun. 26, 1992 [JP] Japan .................... 4-193490
Jun. 26, 1992 [JP] Japan .................... 4-193492

[51] Int. Cl.$^5$ ............................. B01J 13/00
[52] U.S. Cl. .................... 252/315.1; 528/97; 528/110; 528/230; 528/272; 528/300; 528/301; 528/403; 252/315.01; 252/315.4; 252/350; 252/351; 252/352; 252/380
[58] Field of Search ........... 252/350, 351, 352, 380, 252/315.01, 315.1, 315.4; 528/97, 110, 230, 272, 403, 300, 301

[56] References Cited

U.S. PATENT DOCUMENTS

3,846,363 11/1974 Ando et al. ............... 523/164
4,594,167 6/1986 Kobayashi et al. ........ 252/3

FOREIGN PATENT DOCUMENTS

507950 8/1991 European Pat. Off. .
WO-9204352 3/1992 PCT Int'l Appl. .

OTHER PUBLICATIONS

Derwent Publications, Ltd., London, GB, Database WPO, Accession No. 91-314667 week 9143 & JP-A-3210382.

*Primary Examiner*—Samuel A. Acquah
*Attorney, Agent, or Firm*—Larson and Taylor

[57] ABSTRACT

Disclosed are a polyester compound having a repeating unit represented by the formula $$-OC-A-COO-BO- \quad (1)$$

wherein A is a 1,3:2,4-dibenzylidenesorbitol or 1,3:2,4-dibenzylidenexylitol residue of the formula (2)

wherein t is 1 or 0, and B is a residue formed by removal of two hydroxyl groups from a polyhydric alcohol, and an organic gelling agent comprising the polyester compound.

12 Claims, 1 Drawing Sheet

POLYESTER COMPOUNDS AND ORGANIC GELLING AGENTS COMPRISING SAME

FIELD OF THE INVENTION

The present invention relates to thermally reversible polyester type organic gelling agents having good hydrophilic or lipophilic nature. The term "gelling agent" as used herein generally refers to a compound capable of giving a yield point to a system to which it has been applied and causing the fluidity of said system to disappear.

PRIOR ART

Among the thermally reversible low-molecular organic gelling agents so far known, there are dibenzalsorbitol, derivatives thereof having a substituent or substituents on the aromatic nucleus or nuclei, 12-hydroxystearic acid, acylated amino acid amides and cholesterol derivatives, among others. These are used as fluidity modifiers or solidifiers for paints and inks, gelling agents for recovering spilt oils, solidifiers for pesticide formulations, antislumping agents for paintings or adhesive materials, processing aids for macromolecules, solidifiers for perfume formulations, and so forth.

However, the development of thermally reversible gelling agents has not been so marked as compared with thermally irreversible gelling agents which utilize chemical crosslinking reactions.

In particular, in such application fields as gel-forming excipients for cosmetics, drugs and markers in which glycerol, propylene glycol, ethylene glycol or the like is used as a hydrophilic base, or as water-based inks or paints, the development of gelling agents more improved in hydrophilicity is earnestly desired. The situation is the same in the field of printing plates to be prepared from hydrophilic acrylic resins by gel formation followed by ultraviolet curing. On the other hand, there is a demand for hydrophobic gelling agents which can be used for gelling lipophilic inks, coating compositions, polyethylene melt, etc.

Accordingly, it is an object of the invention to provide novel, thermally reversible gelling agents having new characteristics, in particular good hydrophilic or lipophilic nature. To develop such gelling agents greatly contributes to the so-far retarded development of thermally reversible gelling agents and provides novel and useful applications of the same, hence is of great commercial value.

SUMMARY OF THE INVENTION

We made intensive investigations in an attempt to achieve the above object and, as a result, found that polyesters having a specific structure can function as thermally reversible gelling agents with good hydrophilic or lipophilic nature. Based on this finding, we have completed the present invention. So far, in the art, none of compounds having a polyester structure, inclusive of the polyesters of the present invention, have been known to be capable of serving as gelling agents.

The organic gelling agent of the present invention is characterized in that it comprises, as an active ingredient, a polyester compound having a repeating unit of the formula $$—OC—A—COO—BO— \quad (1)$$

wherein A is a dibenzylidenesorbitol or dibenzylidenexylitol residue of the formula

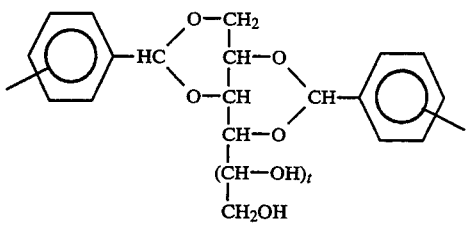

wherein t is 1 or 0, and B is a residue formed by removal of two hydroxyl groups (especially two terminal primary hydroxyl groups) from a polyhydric alcohol.

The present invention further provides a compound of the above formula (1).

Thus, the polyester compound according to the present invention contains structure A, i.e., a structure represented by the formula (2) in the main chain. This structure represented by the formula (2) is known to act as an organic gelling agent. We found that polyester compounds having structure A as incorporated in the main chain function as gelling agents irrespective of the size or kinds of their terminal groups. Thus, the terminal groups of the polyester compound of the formula (1) can be converted in a conventional manner, for example, into an acetyl group, a benzoate group or alkyl ether group (e.g., having 1 to 18 carbon atoms). The present invention has been accomplished based on this novel finding.

In this specification and claims, the term "polyester" is intended to include diesters having two ester groups within the molecule and/or polyesters having more than two ester groups within the molecule.

In the above-mentioned polyester compound of the invention, the number of repetitions of the repeating unit of the formula (1) is not critical. Generally, however, it is recommended that said number be about 1 to 20, preferably about 1 to 10.

In accordance with preferred embodiments of the invention, polyester compounds of the formula (3), (4), (5), (6) and (7) shown below are provided. Formula (3):

wherein A and B are as defined above and $R^1$ is an alkyl group, preferably an alkyl group containing 1 to 20 carbon atoms.

Formula (4):

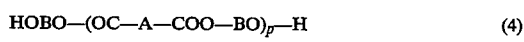

wherein A and B are as defined above and p is an integer of 1 to 20.

Formula (5):

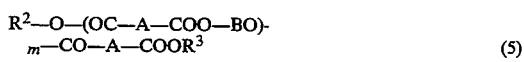

wherein A and B are as defined above, $R^2$ and $R^3$ are the same or different and each is an alkyl group, preferably an alkyl group containing 1 to 20 carbon atoms and m is an integer of 1 to 20.

Formula (6):

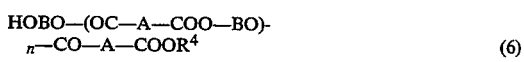

wherein A and B are as defined above, R⁴ is an alkyl group, preferably an alkyl group containing 1 to 20 carbon atoms and n is an integer of 1 to 20.

Among the compound of the above formula (4), polyester compounds of the following formula (7) are readily prepared.

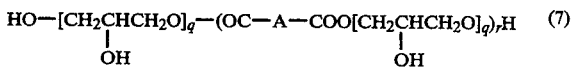

wherein A is as defined above, q is an integer of 1 to 13 and r is an integer of 2 to 10.

The above-mentioned polyester compounds of the invention can be produced in a relatively easy manner, for example in the following manner.

Thus, compounds of the formulas (3) to (7) can be produced by subjecting a 1,3:2,4-bis(alkoxycarbonylbenzylidene)sorbitol compound or a 1,3:2,4-bis(alkoxycarbonylbenzylidene)xylitol compound, each represented by the formula

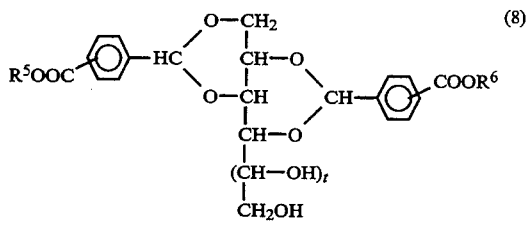

wherein $R^5$ and $R^6$ are the same or different and each is an alkyl group, preferably an alkyl group having 1 to 20 carbon atoms and t is 1 or 0, or a mixture of these, and an excess of a polyhydric alcohol to polycondensation in the presence of a basic catalyst at a temperature of about 20° to 200° C., or alternatively by subjecting a polyhydric alcohol and an equimolar or excess amount of at least one compound of the formula (8) to polycondensation in the presence of a basic catalyst at about 20° to 200° C. This reaction may be carried out in the absence of a solvent or in the presence of a solvent.

The compound of the formula (8) to be used as a starting material of the above reaction can be produced by subjecting sorbitol or xylitol and an alkyl formylbenzoate to condensation under heating in the presence of a solvent and an acid catalyst at a temperature of about 20° to 200° C., as described in EP 507950 A1, for instance. The alkyl formylbenzoate is preferably a formylbenzoic acid C₁-C₂₀ alkyl ester, more preferably methyl p-formylbenzoate. In the reaction for the synthesis of the compound of the formula (8) the alkyl formylbenzoate is used in an amount of about 1 to 3 moles per mole of sorbitol or xylitol. The reaction is carried out in water or in an organic solvent inert to the reaction, such as a hydrocarbon having about 8 to 12 carbon atoms, cyclohexane, or a C₁-C₃ alkyl-substituted cyclohexane. The catalyst is, for example, sulfuric acid or p-toluenesulfonic acid. The reaction time is generally about 2 to 6 hours.

In the thus-obtained compound of the formula (8), the position of the ester group on the benzene ring may be ortho, meta or para. As R⁵ and R⁶, there may be mentioned alkyl groups such as methyl, ethyl, propyl, butyl, octyl, dodecyl or stearyl, among others. 1,3:2,4-bis(methoxycarbonylbenzylidene)-sorbitol, 1,3:2,4-bis(methoxycarbonylbenzylidene)xylitol or a mixture of these are preferred examples of the compound of the formula (8). In the present invention, the compounds of the formula (8) may be used singly or at least two of them may be used in combination.

The polyhydric alcohols to be used are those corresponding to B in the above formula (1). Preferred examples of the polyhydric alcohol are ethylene glycol; diethylene glycol and other polyethylene glycol oligomers, in particular polyethylene glycols having a polymerization degree of about 2 to about 1,000, preferably polyethylene glycols having a polymerization degree of about 3 to about 200; propylene glycol; dipropylene glycol and other polypropylene glycol oligomers, in particular polypropylene glycols having a polymerization degree of 2 to about 1,000, preferably polypropylene glycols having a polymerization degree of about 3 to about 200; butanediols; pentanediols; hexamethylene glycol; xylylene glycols and nuclear hydrogenation products thereof, and ethylene oxide adducts of xylylene gylcols or nuclear hydrogenation products thereof (the number of moles of ethylene oxide added=about 1-50); bisphenol A, nuclear hydrogenation products thereof, and ethylene oxide adducts of bisphenol A or nuclear hydrogenation products thereof (the number of moles of ethylene oxide added=about 1-50); glycerol, diglycerol, triglycerol, other polyglycerol oligomers, preferably polyglycerol oligomers having a polymerization degree of about 2 to about 20; and like polyols; polyethylenes having a hydroxyl group at each of terminal α- and ω-positions (number average molecular weight Mn=up to about 10,000, particularly about 200 to about 4000); polybutadienes having a hydroxyl group at each of both termini (Mn=up to about 10,000, particularly about 200 to about 4000); hydrogenated polybutadienes having a hydroxyl group at each of both termini (Mn=up to about 10,000, particularly about 200 to about 4000); polyisoprenes having a hydroxyl group at each of both termini (Mn=up to about 10,000, particularly about 200 to about 4000); hydrogenated polyisoprenes having a hydroxyl group at each of both termini (Mn=up to about 10,000, particularly about 200 to about 4000) or the like. These may be used either singly or in combination (as a mixture of two or more).

For producing a compound of the formula (7), in particular, glycerol or a polyglycerol oligomer of the formula

wherein q is an integer of 1 to 13, is used as the polyol. The compounds of the formula (9) are known and readily available.

When, among these polyhydric alcohols, those polyhydric alcohols that have at least two primary hydroxyl groups and at least one secondary hydroxyl group are used for preparing a linear polyester by polycondensation, there is a general tendency that the primary hydroxyl groups alone are involved in the reaction while the secondary hydroxyl group or groups are not involved in the reaction, since the reactivity of the primary hydroxyl groups is very high as compared with the secondary hydroxyl groups; hence protection of the secondary hydroxyl group(s) is not required. Therefore, when a polyol of the above formula (9), for instance, is used, it can in effect function as a divalent primary alcohol and can generally be subjected to the reaction without protecting its secondary hydroxyl group or groups, to readily give polyester compounds of the above formula (7).

The polyesterification reaction can give, in high yields, polyester type gelling agents of the formula (1) having the desired structure depending on the charged monomer ratio between the compound of the formula (8), which is a dibasic carboxylic acid ester, and the polyhydric alcohol. Thus, when the polyhydric alcohol is used in an amount larger than the equimolar amount, a compound of the formula (4) wherein p is small, e.g., diester (p=1), tetraester (p=2) and like low-molecular-weight polyester are formed in increased yields, with a tendency that the molecular weight of the product polyester decreases.

Conversely, when the compound of the formula (8) is used in an amount larger than the equimolar amount, the product is a mixture of compounds of the formulas (4), (5) and (6), and with the increase in the amount of the compound of the formula (8), a compound of the formula (5) tends to be formed in an increased amount. For increasing the molecular weight of the polyester, it is advisable that the charged monomer ratio be as close as possible to the stoichiometric one and that the raw materials have high purity. The compound of the formula (3) is relatively easily formed by terminating the reaction for forming the compound of the formula (4) or (5) at an early stage thereof, or by using a polyhydric alcohol having large molecular weight in a reaction with the compound of the formula (8) by ester interchange.

Generally, the molecular weight of the compound of the formulas (3) to (7) depends on the purity of the raw materials and solvent used, reaction temperature, feed monomer ratio of the polyhydric alcohol to the compound of the formula (8), more particularly a ratio of the total number of moles of the primary hydroxyl groups contained in the polyhydric alcohol fed to the total number of moles of the ester groups contained in the compound of the formula (8) fed (this monomer ratio will hereinafter referred to as "primary OH/ester group monomer ratio"), etc. The molecular weight of the polyester compound to be obtained tends to increase with an increase in the purity of the starting materials and solvent used, and with an increase in the reaction temperature, and when said primary OH/ester group monomer ratio is as close as 1.

On the other hand, whether the polyester compound to be formed has at its terminal ends a hydroxyl group(s) or an alkyl group(s) derived from the compound of the formula (8) used is largely dependent on primary OH/ester group monomer ratio. Although variable depending on the kinds of starting materials used, when primary OH/ester group monomer ratio is by far larger than 1, the polyester compound to be obtained at the end point of the reaction generally tends to have a hydroxyl group at each of both termini as in the compound of the formula (4). When primary OH/ester group monomer ratio is slightly larger or slightly smaller than 1 or substantially equal to 1, the polyester compound to be obtained generally tends to be a compound having a hydroxyl group at one of its termininal ends and an alkyl group at the other as in the compound of the formula (6), in admixture with a compound having a hydroxyl group at each of its both termini as in the compound of the formula (4) and a compound having an alkyl group at each of its both termini as in the compound of the formula (5). When primary OH/ester group monomer ratio is by far smaller than 1, the polyester compound to be obtained generally tends to have an alkyl group at each of both termini as in the compound of the formula (5).

Thus, the desired polyesters can be readily obtained if the relation of the primary OH/ester group monomer ratio, purity of the starting materials and reaction temperature, on one hand, and the molecular weight or terminal structure of the product polyester, on the other hand, has been determined in advance.

Generally, the amount of the polyhydric alcohol is not critical but can suitably be selected according to the desired structure of the polyester compound to be obtained. However, when the production of the polyester of the formula (4) is intended, it is recommendable to use the polyhydric alcohol in an amount of about 2 to about 150 moles, preferably about 20 to about 80 moles, per mole of the monomer of the formula (8). When the polyhydric alcohol is used in excess, the excess polyhydric alcohol may also serve as a reaction solvent.

When the production of the compound of the formula (5) is intended, it is recommended to use the monomer of the formula (8) in an amount of about 2.0 to about 20 moles, preferably about 3 to about 10 moles, per mole of the polyhydric alcohol.

When the production of the compound of the formula (6) is intended, it is recommended to use the monomer of the formula (8) in an amount of about 0.2 to about 2.0 moles, preferably about 0.5 to about 1.8 moles, per mole of the polyhydric alcohol. However, in this case, it is generally difficult to completely prevent the concurrent formation of the compounds of the formulas (4) and (5).

The basic catalyst is, for example, an alkali metal such as lithium, sodium or potassium, an alkali metal hydride such as lithium hydride, sodium hydride or potassium hydride, a metal alcoholate such as sodium methylate, sodium ethylate or potassium tert-butylate, a metal amide such as sodium amide or diisopropyllithiumamide, or any other neutral or alkaline catalyst which is conventionally used in esterification reactions (e.g titanium alcoholate, aluminum hydroxide, tin oxide). The catalyst is generally used in an amount of about 0.01 to 10 moles per mole of the monomer of the formula (8).

This reaction for synthesizing the polyester compound of the invention can be conduted in the absence of solvent, but may be carried out in a solvent if so desired. Any of those solvents which dissolve the monomer of the formula (8) and polyhydric alcohol and will not adversely affect the reaction can be used as said solvent. Typical examples of such solvent are ethers such as tetrahydrofuran and dioxane, hydrocarbon solvents such as benzene, toluene, n-hexane and cyclohexane, and aprotic polar solvents such as dimethyl sulfoxide, dimethylformamide, N-methyl-2-pyrrolidone, N,N-dimetylacetamide or a mixture of these. The amount of such solvent to be used is not particularly limited and may range from about 200 to about 5000 parts by weight, per 100 parts by weight of the monomer of the formula (8).

The reaction temperature is about 0° to 200° C., preferably about 20° to 180° C. The reaction time is about 1 to 20 hours, preferably about 3 to 10 hours. When necessary, the reaction may be conducted in an inert gas atmosphere such as a nitrogen gas atmosphere.

The thus-obtained reaction mixture is generally in the form of a uniform homogeneous liquid while under heating but, when cooled to room temperature, becomes a gel-like solid. This is dispersed in and neutralized with an appropriate neutralizing agent solution, for example a weakly acidic aqueous solution of acetic acid, an aqueous solution of phosphoric acid or a solution of propionic acid in methanol. The crude product obtained is washed with water and dried to give the compound of formula (3), formula (4) (particularly formula (7)), formula(5) or forumula (6) in a purified form.

If desired, the product can be further purified to isolate the respective compounds of the formulas (3)–(7) by a conventional separation and purification method such as chromatography. However, any of the compounds of the formulas (3)–(7) can be used singly or in any suitable combination and in each case gives the desired gelling effect. Therefore, they need not to be separated into the respective compounds.

The thus-obtained compounds of formula (3), (4), (5), (6) or (7) generally have a melting point of up to about 260° C. and are useful as gelling agents having good low-temperature meltability.

The polyester compounds of the invention are useful in the same applications as the conventional gelling agents, for example in fluidity adjustment or rheology modification or solidification of paints and inks, recovering spilt oils by gelation, and preventing paintings from sagging and preventing adhesives from slumping, and are also useful as polymer processing aids and solidifiers for perfume formulations.

The compounds of the invention having terminal long-chain alkyl group(s) or long-chain hydrocarbon group within the moiety represented by B or the compound of the invention containing polyoxypropylene chain units are generally lipophilic and useful for gelling lipophilic substances. The compounds of the invention containing a large amount of hydroxyl groups such as a compound of the formula (7) and the compounds of the invention containing polyoxyethylene chain units or containing glycerol or polyglycerol chain units are hydrophilic and useful for gelling hydrophilic substances.

In particular, the polyesters of the invention have a characteristic feature in that when they are added to hydrophilic substances such as glycerol, propylene glycol and ethylene glycol or to lipophilic substances such as a lipophilic ink, a coating composition or a molten resin, in a small amount, and the resulting mixture is heated for dissolution and then cooled, the whole mixtures can readily turn into gels. The amount of said polyester to be added to such hydrophilic or lipophilic substances is not critical provided that the desired effect can be produced, and is generally not more than 20% by weight, preferably not more than 15% by weight, especially about 1 to 10% by weight, based on the hydrophilic or lipophilic substance. The gels formed are thermally reversible gels, namely they turn into sol upon heating and into gel upon cooling. The polyesters of the invention may be used in combination with the conventional thermally-reversible gelling agents, if so desired.

The polyesters of the invention are useful not only as gelling agents but also as antistatic, anti fogging and/or antifouling agents or printability modifiers for polyolefin resins. They are also useful as nucleating agents functioning to promote the crystallization and improving the rigidity of crystalline macromolecules such as polyethylene, polypropylene, polyethylene terephthalate and polybutadiene resins. They are further useful as plasticizers for improving the moldability of compositions comprising such crystalline resins without substantially impairing the characteristics thereof.

The following examples illustrate the invention in further detail. Gel forming ability evaluation was carried out by the following method.

Gel formation evaluation: To 10 g of a target substance (glycerol or ethylene glycol) was added 0.3 g of a polyester (mixture) of the invention. The resulting mixture was heated to produce a one-phase homogeneous solution state. The mixture was then cooled with water and allowed to stand at room temperature for 5 minutes. Then, a load of 80 g/cm$^2$ is applied to the mixture by means of a glass rod, and judgment is made as to whether the glass rod can penetrate into the mixture.

Figure 2:
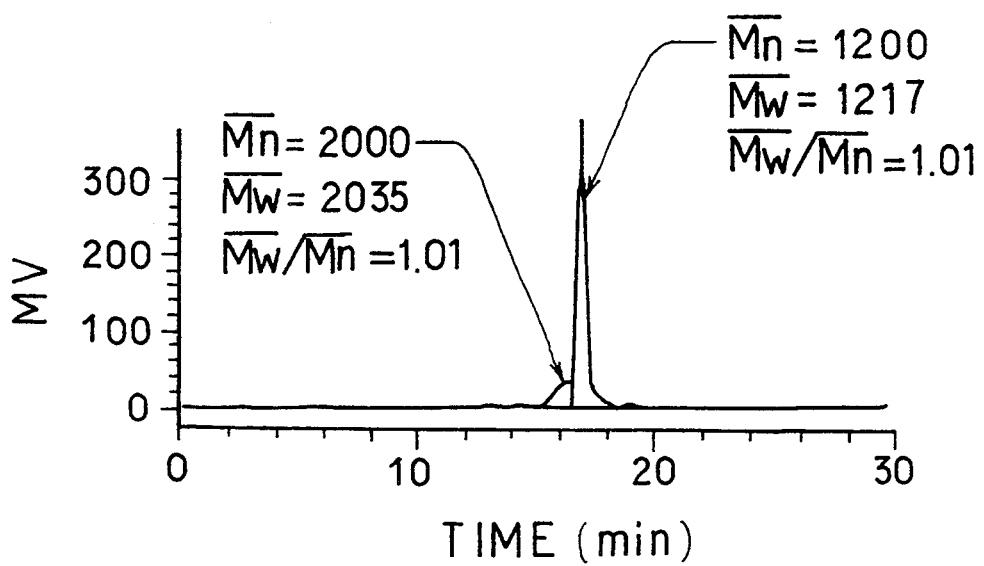

FIG. 1 and FIG. 2 show GPC charts recorded with the polyester compounds obtained in Example 8 and Example 9, respectively.

EXAMPLE 1

A 500-ml separable flask equipped with a thermometer, a stirrer and a decanter having a condenser was charged with 9.5 g (0.02 mole) of 1,3:2,4-bis(p-methyloxycarbonylbenzylidene)sorbitol, 96 g (0.4 mole) of triglycerol and 1.6 g of a 28% sodium methylate solution in methanol and the mixture was heated at an oil bath temperature of 160° C. for 8 hours with stirring. Then, after cooling to room temperature, the resultant gel-like solid was dispersed in 1 liter of a weakly acidic aqueous solution of acetic acid and collected by filtration. The crude product obtained was washed with water and dried at 90° C. under ordinary pressure for 6 hours to give 12 g of a white solid. Analysis by gel permeation chromatography (hereinafter referred to as "GPC") revealed that the product was a mixture of a tetraester (in the formula (4), p=2, B=triglycerol residue; hereinafter referred to as "polyester (a)") and a hexaester (in the formula (4), p= 3, B=triglycerol residue; hereinafter referred to as "polyester (b)") (weight ratio: (a)/(b)=6/1).

The following FT-IR spectrum data were obtained with the above product:

FT-IR (KBr): 3300, 2928, 1718, 1614, 1578, 1285, 1155, 1090, 850, 750 cm$^{-1}$

Melting point (°C.): 140–165.

The above mixture was subjected to gel formation evaluation. With each target substance, gel formation was observed with a gel strength of not less than 80 g/cm$^2$, without allowing glass rod penetration.

EXAMPLE 2

The procedure of Example 1 was followed with the exception of using an oil bath temperature of 200° C. in lieu of 160° C., thereby giving 10 g of a white solid. GPC analysis revealed that the product obtained was a mixture of polyester (a) and polyester (b) (weight ratio: (a)/(b)=⅓).

The following FT-IR spectrum data were obtained with the above product:

FT-IR (KBr):3295, 2930, 1725, 1615, 1580, 1280, 1160, 1085, 854, 745 cm$^{-1}$

Melting point (°C.): 130–150.

The above mixture was subjected to gel formation evaluation. With each target substance, gel formation was observed with a gel strength of not less than 80 g/cm$^2$, without allowing glass rod penetration.

EXAMPLE 3

The procedure of Example 1 was followed with the exception of using 42.4 g (0.4 mole) of diethylene glycol in lieu of 96 g of triglycerol, thereby giving 9.8 g of a white solid. GPC analysis revealed that the product was a mixture of a tetraester (in the formula (4), p=2, B=diethylene glycol residue; hereinafter referred to as "polyester (c)"), a hexaester (in the formula (4), p=3, B=diethylene glycol residue; hereinafter referred to as "polyester (d)") and an octaester (in the formula (4), p=4, B=diethylene glycol residue; hereinafter referred to as "polyester (e)") (weight ratio: (c)/(d)/(e)=2/1/1/).

The following FT-IR spectrum data were obtained with the above product.

FT-IR (KBr): 3258, 2878, 1724, 1615, 1580, 1514, 1283, 1168, 1095, 875, 752, 710 cm$^{-1}$

Melting point (°C.): 150-170.

The above mixture was subjected to gel formation evaluation with each target substance, gel formation was observed with a gel strength of not less than 80 g/cm$^2$, without allowing glass rod penetration.

EXAMPLE 4

The procedure of Example 1 was followed with the exception of using 47.2 g (0.4 mole) of 1,6-hexanediol in lieu of 96 g of triglycerol, thereby giving 10.5 g of a white solid. GPC analysis revealed that the product was a mixture of a tetraester (in the formula (4), p=2, B=1,6-hexanediol residue; hereinafter referred to as "polyester (f)"), a hexaester (in the formula (4), p=3, B=1,6-hexanediol residue; hereinafter referred to as "polyester (g)") and an octaester (in the formula (4), p=4, B=1,6-hexanediol residue; hereinafter referred to as "polyester (h)")(weight ratio: (f)/(g)/(h)=1/2/1).

The following spectral data were obtained with the above product:

FT-IR (KBr): 3243, 2876, 1723, 1615, 1580, 1279, 1098, 854, 751 cm$^{-1}$

Melting point (°C.): 130-145.

The above mixture was subjected to gel formation evaluation. With each target substance, gel formation was observed with a gel strength of not less than 80 g/cm$^2$, without allowing glass rod penetration.

EXAMPLE 5

The procedure of Example 1 was followed with the exception of using 53.6 g (0.4 mole) of dipropylene glycol in lieu of 96 g of triglycerol, thereby giving 11.4 g of a white solid. GPC analysis revealed that this product was a mixture of a tetraester (in the formula (4), p=2, B= dipropylene glycol residue; hereinafter referred to as "polyester (i)") and a hexaester (in the formula (4), p=3, B=dipropylene glycol residue; hereinafter referred to as "polyester (j)") (weight ratio: (i)/(j)=4/1).

The following spectral data were obtained with the above product:

FT-IR (KBr): 3270, 2877, 1718, 1616, 1579, 1278, 1094, 1020, 831, 750 cm$^{-1}$

Melting point (°C.): 130-140.

This mixture was subjected to gel formation evaluation. With each target subject, gel formation was observed with a gel strength of not less than 80 g/cm$^2$, without allowing glass rod penetration.

EXAMPLE 6

The procedure of Example 1 was followed with the exception of using 303 g of decaglycerol (average polymerization degree 10) in lieu of 93 g of triglycerol, thereby giving 30 g of a white solid. GPC analysis revealed that this product was a polyester of formula (4) wherein the average of p=16 and B is a decaglycerol residue.

The following spectral data were obtained with the above product:

FT-IR (KBr): 3250, 2978, 1725, 1615, 1580, 1276, 1094, 1020, 857, 752 cm$^{-1}$

Melting point (°C.): 50-60

This mixture product was subjected to gel formation evaluation. With each target substance, gel formation was observed with a gel strength of not less than 80 g/cm$^2$, without allowing glass rod penetration.

EXAMPLE 7

The same apparatus as used in Example 1 was charged with 4 g (0.084 mole) of 1,3:2,4-bis(p-methyloxycarbonylbenzylidene)sorbitol, 25 g of polyethylene glycol #4000 (average molecular weight 2879, Mw/Mn=1.02), 7 g of potassium carbonate and 100 ml of dimethyl sulfoxide, and the mixture was heated at 140° C. for 8 hours with stirring. After cooling to room temperature, the potassium carbonate was filtered off. The filtrate was added dropwise to 500 ml of isopropanol and the resultant precipitate was collected by filtration and dried to give 20 g of a white solid. GPC analysis revealed that this was a monoesterified product represented by the formula (3) (Mw 3284, Mw/Mn=1.04) wherein R$^1$ is methyl and B is a polyethylene glycol residue.

The following FT-IR spectrum data were obtained with said product:

FT-IR (KBr): 2882, 1718, 1599, 1558, 1280, 1242, 1114, 964, 844, 711 cm$^{-1}$.

Melting point (°C.): 50-68.

This mixture product was subjected to gel formation evaluation. With each target substance, gel formation was observed with a gel strength of not less than 80 g/cm$^2$, without allowing glass rod penetration.

EXAMPLE 8

A 500-ml separable flask equipped with a thermometer, a stirrer and a decanter having a condenser was charged with 9.5 g (0.02 mole) of 1,3:2,4-bis (p-methoxycarbonylbenzylidene)sorbitol, 55 g (0.6 mole) of glycerol and 1.6 g of a 28% sodium methylate solution in methanol, and the mixture was heated at an oil bath temperature of 160° C. for 8 hours with stirring. After cooling to room temperature, the reaction mixture was poured into 1 liter of a weakly acidic aqueous solution of acetic acid for dispersing the resultant gel-like solid therein. The crude solid product was collected by filtration, washed with water and dried at 90° C. under ordinary pressure for 6 hours to give 12 g of a white solid. GPC analysis revealed that the main products were polyesters of the formula (7) in which q=1 and r=2 to 3 (theoretical molecular weight=1096 (q=1, r=2), 1598 (q=1, r=3)). A GPC chart of said white solid is shown in FIG. 1.

The GPC analysis was carried out under the following conditions. A molecular weight calibration curve was constructed using polyethylene glycols for GPC calibration curve construction.

Column: Shodex GPC KD803+802
Mobile phase: DMF
Flow rate: 1 ml/min
Pressure: 54 Kg/cm$^2$
Detector: RI
Temperature: 40° C.

The following FT-IR spectrum data were obtained with said white solid:

FT-IR (KBr): 3285, 2938, 1723, 1615, 1580, 1283, 1167, 1095, 856, 752, 711 cm$^{-1}$

Melting point (°C.): 220-240.

EXAMPLE 9

The procedure of Example 8 was followed with the exception of using 100 g (0.6 mole) of diglycerol in lieu of 55 g of glycerol (0.6 mole), thereby giving 13 g of a white solid. GPC analysis revealed that the main products were polyesters of the formula (7) wherein q=2 and r=2 to 3 (theoretical molecular weight=1318 (q=2, r=2), 1894 (q=2, r=3)). A GPC chart of said white solid is shown in FIG. 2.

The following FT-IR spectrum data were obtained with said solid:

FT-IR (KBr): 3304, 2932, 1724, 1615, 1582, 1282, 1165, 1096, 856, 752 cm$^{-1}$.

Melting point (°C.): 180-200.

EXAMPLE 10

The procedure of Example 8 was followed with the exception of using 144 g (0.6 mole) of triglycerol in lieu of 55 g (0.6 mole) of glycerol, thereby giving 12.6 g of a white solid. GPC analysis gave a GPC chart similar in pattern to that obtained in Example 8, indicating that the main products were polyesters of the formula (7) wherein q=3 and r=5 to 7.

The following FT-IR spectrum data were obtained with said white solid:

FT-IR (KBr): 3298, 2930, 1720, 1615, 1580, 1280, 1160, 1095, 854, 750 cm$^{-1}$

Melting point (°C.): 140-160.

EXAMPLE 11

The procedure of Example 8 was followed with the exception of using 277 g (0.6 mole) of hexaglycerol (average polymerization degree (q)=6) in lieu of 55 g (0.6 mole) of glycerol, thereby giving a gel-like solid. This solid was dispersed in 1 liter of acetone. Decantation gave 14 g of a white syrup-like substance. GPC analysis revealed that the main products were polyesters of the formula (7) wherein q=6 and r=5 to 7.

The following FT-IR spectrum data were obtained:

FT-IR (KBr): 3295, 2928, 1718, 1614, 1580, 1278, 1165, 1094, 855, 750 cm$^{-1}$

APPLICATION EXAMPLE 1

The compounds of the invention as obtained in Examples 8 to 11 (0.7 g each) were respectively added to 50 g each of ethylene glycol, glycerol and diethylene glycol maintained at 130° C. Each mixture was heated for 5 minutes with stirring and then cooled to room temperature. For each compound and in each case, gel forming ability was observed.

EXAMPLE 12

A 1000-ml separable flask equipped with a thermometer, a stirrer and a decanter having a condenser was charged with 500 ml of N-methyl-2-pyrrolidone. Then, 210.0 g (0.22 mole) of bis(octadecyloxycarbonylbenzylidene)sorbitol and 12.4 g (0.2 mole) of ethylene glycol were added thereto, and the mixture was heated to 100° C. Then, 2.1 g of sodium methylate was added and stirring was continued for 8 hours.

The reaction product was neutralized and separated in the same manner as in Example 1 and dried, giving 215 g of a white solid. GPC analysis revealed that the product was a mixture of a compounds of the formula (4) wherein B is an ethylene glycol residue and p is 1 to 3, a compound of the formula (5) wherein R$^2$=R$^3$=octadecyl, B is an ethylene glycol residue and m is 1 to 3 and a compound of the formula (6) wherein R$^4$=octadecyl, B is an ethylene glycol residue and n is 1 to 3 (weight ratio of the compound (4): compound (5): compound (6)=1:1:2)

Melting point (°C.): 130-135

This mixture product was subjected to gel formation evaluation. With each target substance, gel formation was observed with a gel strength of not less than 80 g/cm$^2$, without allowing glass rod penetration.

What is claimed is:

1. A polyester compound having a repeating unit represented by the formula

$$-OC-A-COO-BO- \quad (1)$$

wherein A is a 1,3:2,4-dibenzylidenesorbitol or 1,3:2,4-dibenzylidenexylitol residue represented by the formula

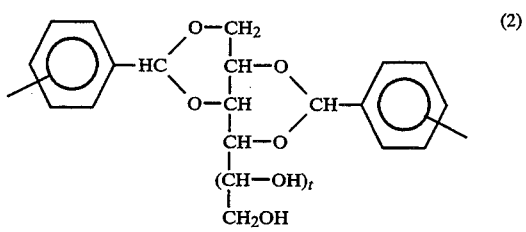

(2)

wherein t is 1 or 0, and B is a residue formed by removal of two hydroxyl groups from a polyhydric alcohol.

2. A polyester compound as claimed in claim 1 which is represented by the formula $$R^1OOC-A-COO-BOH \quad (3)$$

wherein A and B are as defined in claim 1 and R$^1$ is an alkyl group having 1 to 20 carbon atoms.

3. A polyester compound as claimed in claim 1 which is represented by the formula $$HOBO-(OC-A-COO-BO)_p-H \quad (4)$$

wherein A and B are as defined in claim 1 and p is an integer of 1 to 20.

4. A polyester compound as claimed in claim 1 which is represented by the formula $$R^2-O-(OC-A-COO-BO)\text{-}_m-CO-A-COOR^3 \quad (5)$$

wherein A and B are as defined in claim 1, R$^2$ and R$^3$ are the same or different and each is an alkyl group having 1 to 20 carbon atoms and m is an integer of 1 to 20.

5. A polyester compound as claimed in claim 1 which is represented by the formula $$HOBO-(OC-A-COO-BO)\text{-}_n-CO-A-COOR^4 \quad (6)$$

wherein A and B are as defined in claim 1, $R^4$ is an alkyl group having 1 to 20 carbon atoms and n is an integer of 1 to 20.

6. A polyester compound as claimed in claim 1 which is represented by the formula

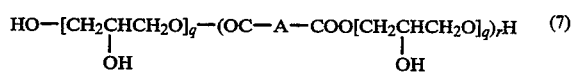

wherein A is as defined in claim 1, q is an integer of 1 to 13 and r is an integer of 2 to 10.

7. An organic gelling agent which comprises a polyester compound having a repeating unit represented by the formula

wherein A is a 1,3:2,4-dibenzylidenesorbitol or 1,3:2,4-dibenzylidenexylitol residue represented by the formula

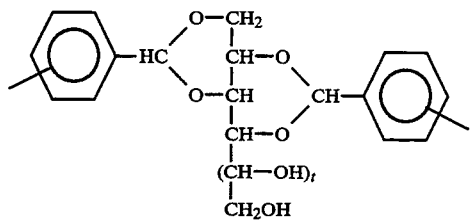

wherein t is 1 or 0, and B is a residue formed by removal of two hydroxyl groups from a polyhydric alcohol.

8. An organic gelling agent as claimed in claim 7, wherein said polyester compound is represented by the formula

wherein A and B are as defined in claim 7 and $R^1$ is an alkyl group having 1 to 20 carbon atoms.

9. An organic gelling agent as claimed in claim 7, wherein said polyester compound is represented by the formula

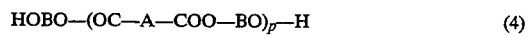

wherein A and B are as defined in claim 7 and p is an integer of 1 to 20.

10. An organic gelling agent as claimed in claim 7, wherein said polyester compound is represented by the formula

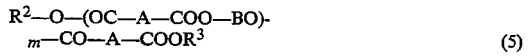

wherein A and B are as defined in claim 7, $R^2$ and $R^3$ are the same or different and each is an alkyl group having 1 to 20 carbon atoms and m is an integer of 1 to 20.

11. An organic gelling agent as claimed in claim 7, wherein said polyester compound is represented by the formula

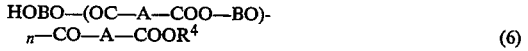

wherein A and B are as defined in claim 7, $R^4$ is an alkyl group having 1 to 20 carbon atoms and n is an integer of 1 to 20.

12. An organic gelling agent as claimed in claim 7, wherein said polyester compound is represented by the formula

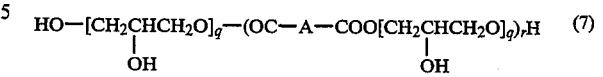

wherein A is as defined in claim 7, q is an integer of 1 to 13 and r is an integer of 2 to 10.

* * * * *